United States Patent
Fujita et al.

(10) Patent No.: US 7,893,274 B2
(45) Date of Patent: Feb. 22, 2011

(54) PROCESS FOR PRODUCING AMINO ACID N-CARBOXYANHYDRIDE

(75) Inventors: Yukihiro Fujita, Chiba (JP); Takeshi Endo, Kanagawa (JP); Haruo Nishida, Fukuoka (JP); Atsushi Sudo, Fukuoka (JP)

(73) Assignee: JSR Corporation, Tokyo (JP)

( * ) Notice: Subject to any disclaimer, the term of this patent is extended or adjusted under 35 U.S.C. 154(b) by 1229 days.

(21) Appl. No.: 11/457,035

(22) Filed: Jul. 12, 2006

(65) Prior Publication Data

US 2007/0015932 A1 Jan. 18, 2007

(30) Foreign Application Priority Data

Jul. 13, 2005 (JP) .............................. 2005-203769

(51) Int. Cl.
*C07D 263/00* (2006.01)
(52) U.S. Cl. ..................................... 548/227
(58) Field of Classification Search .................. 548/227
See application file for complete search history.

(56) References Cited

U.S. PATENT DOCUMENTS 5,028,693 A * 7/1991 Fuller et al. ................. 530/335
5,359,086 A    10/1994 Merslavic et al.

FOREIGN PATENT DOCUMENTS

| JP | 11-29560 | 2/1999 |
|---|---|---|
| JP | 2000-327666 | 11/2000 |
| JP | 2002-322160 | 11/2002 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hélène Collet, et al., A New Simple and Quantitative Synthesis of α-Aminoacid-N-Carboxyanhydrides (oxazolidines-2,5-dione), Tetrahedron Letters, vol. 37, No. 50, 1996, pp. 9043-9046.
Jun-ichi Yamaguchi, et al., "Condensation of α-Amino Acid with Amine in the Absense of a Coupling Agent", Chemistry Letters, vol. 32, No. 9, 2003, pp. 830-831.
Atsushi Nagai, et al., "A Facile Synthesis of *N*-Carboxyanhydrides and Poly (α-amino acid) Using Di-*tert*-butyltricarbonate", Macromolecules, vol. 37, No. 7, 2004, pp. 2332-2334.

* cited by examiner

*Primary Examiner*—James O Wilson
*Assistant Examiner*—Douglas M Willis
(74) *Attorney, Agent, or Firm*—Oblon, Spivak, McClelland, Maier & Neustadt, L.L.P.

(57) ABSTRACT

The present invention provides a process for producing an amino acid N-carboxyanhydride, which comprises reacting an amino acid or a derivative thereof with a compound represented by the following formula (1):

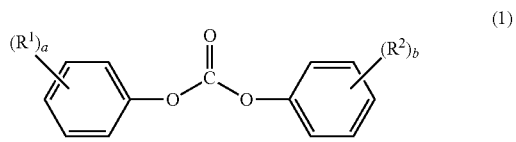

wherein $R^1$ and $R^2$ represent the same or different electron-withdrawing substituents and each independently are an optionally substituted acyl group, an optionally substituted alkyloxycarbonyl group, an optionally substituted perfluoroalkyl group, an optionally substituted perchloroalkyl group, a cyano group, a halogen atom, or a nitro group; and a and b are the same or different and each are an integer of 1-5.

14 Claims, No Drawings

PROCESS FOR PRODUCING AMINO ACID N-CARBOXYANHYDRIDE

FIELD OF THE INVENTION

The present invention relates to a process for producing an amino acid N-carboxyanhydride. More particularly, the invention relates to a process for safely producing an amino acid N-carboxyanhydride in a high yield without using phosgene.

BACKGROUND OF THE INVENTION

Amino acid N-carboxyanhydrides are used as intermediate raw materials for obtaining polypeptides from amino acids.

Generally known methods for synthesizing an amino acid N-carboxyanhydride are the method found by Leuchs in 1906 (*Ber. Dtsch. Chem. Ges.*, 1906, 39, 857-859), the method proposed by Curtius et al. (*J. Prakt. Chem.*, 1930, 125, 211-302), and the Fuchs-Farthing method (*Nature* (London), 1950, 165, 647; *J. Chem. Soc.*, 1951, 3218-3222). Mainly used of these is the Fuchs-Farthing method, in which an amino acid N-carboxyanhydride is obtained in a high yield by the reaction of an amino acid with phosgene.

However, since phosgene is an exceedingly toxic gas, great care should be taken in handling this compound from the standpoints of environmental problem and safety. Use of phosgene is hence severely restricted and the industrial utilization of amino acid N-carboxyanhydrides is hence limited.

There are the following several investigations concerning techniques for synthesizing an amino acid N-carboxyanhydride without using phosgene.

(I) A method in which an amino acid N-carboxyanhydride is produced by reacting an amino acid with N,N-carbonyldiimidazole (patent document 1: U.S. Pat. No. 5,359,086).

(II) A method in which an amino acid N-carboxyanhydride is produced by reacting an N-carbamoylamino acid with an $NO/O_2$ mixed gas (non-patent document 1: *Tetrahedron Letters*, 1996, 37, 9043).

(III) A method in which an amino acid N-carboxyanhydride is produced by reacting an amino acid with carbon dioxide in a supercritical state (patent document 2: JP-A-11-29560)

(IV) A method in which an amino acid N-carboxyanhydride is produced by reacting an aldehyde with carbon monoxide in the presence of a transition metal catalyst (patent document 3: JP-A-2000-327666).

(V) A method in which an amino acid N-carboxyanhydride is produced by reacting an amino acid with di-tert-butyl tricarbonate (patent document 4: JP-A-2002-322160; non-patent document 3: *Macromolecules*, 2004, 37, 251).

(VI) A method which comprises reacting N-nitrophenyl chloroformate with N-hydroxysuccinimide, reacting the resultant N-(4-nitrophenoxycarbonyloxy)succinimide with an amino acid to obtain an N-(4-nitrophenoxycarbonyl) amino acid, and synthesizing an amino acid amide from the N-(4-nitrophenoxycarbonyl)amino acid via an amino acid N-carboxyanhydride as an intermediate (non-patent document 2: *Chemistry Letters*, 2003, 32, 830).

However, those methods have the following drawbacks Method (I) is a case in which N-[1(S)-ethoxycarbonyl-3-phenylpropyl]-L-alanine N-carboxyanhydride was synthesized as an intermediate for an angiotension converting enzyme inhibitor by reacting N-[1(S)-ethoxycarbonyl-3-phenylpropyl]-L-alanine with N,N-carbonyldiimidazole There are unsolved problems concerning this method that the amino acid N-carboxyanhydride was not isolated and that N-[1(S)-ethoxycarbonyl-3-phenylpropyl]-L-alanine was the only amino acid actually used. Method (II) is industrially accompanied by a drawback because the target compound is produced via an exceedingly dangerous nitrosourea compound as an intermediate. Method (III) is not practical because it necessitates a large-scale apparatus for forming a supercritical state. Method (IV) has an unsolved problem that an optically active amino acid N-carboxyanhydride cannot be obtained. Method (V) has an unsolved problem concerning industrial use thereof because phosgene or triphosgene, which is toxic like phosgene, is presently used for synthesizing the di-tert-butyl tricarbonate. Method (VI) employs phosgene as a raw material for synthesizing the N-nitrophenyl chloroformate. Furthermore, the amino acid N-carboxyanhydride as an intermediate was not isolated.

As described above, those known methods have problems, for example, that a highly toxic raw material is used and an optically active amino acid N-carboxyanhydride cannot be obtained. There has been no known method for amino acid N-carboxyanhydride synthesis which is free from these problems.

Patent Document 1: U.S. Pat. No. 5,359,086

Non-Patent Document 1: Tetrahedron Letters, 1996, 371, 9043.

Patent Document 2: JP-A-11-29560

Patent Document 3: JP-A-2000-327666

Patent Document 4: JP-A-2002-322160

Non-Patent Document 2: *Chemistry Letters*, 2003, 32, 830.

Non-Patent Document 3: *Macromolecules*, 2004, 37, 2332.

SUMMARY OF THE INVENTION

An object of the invention is to provide a process which is useful for producing an amino acid N-carboxyanhydride without using phosgene and is industrially applicable.

Other objects and effects of the invention will become apparent from the following description.

The invention provides a process for producing an amino acid N-carboxyanhydride, which comprises reacting an amino acid or a derivative thereof with a compound represented by the following formula (1):

$$(R^1)_a \text{---} \phantom{xx} \text{---} O \text{---} \underset{\underset{O}{\parallel}}{C} \text{---} O \text{---} \phantom{xx} \text{---} (R^2)_b \quad (1)$$

wherein $R^1$ and $R^2$ represent the same or different electron-withdrawing substituents and each independently are an optionally substituted acyl group, an optionally substituted alkyloxycarbonyl group, an optionally substituted perfluoroalkyl group, an optionally substituted perchloroalkyl group, a cyano group, a halogen atom, or a nitro group; and a and b are the same or different and each are an integer of 1-5.

The invention further provides a process for producing an amino acid N-carboxyanhydride which comprises:

reacting the compound represented by formula (1) given above with an amino acid ester represented by the following formula (2):

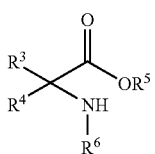

(2)

wherein $R^3$ and $R^4$ each independently represent a hydrogen atom, an optionally substituted alkyl group, an optionally substituted cycloalkyl group, an optionally substituted aryl group, or an optionally substituted heterocycle, provided that $R^3$ and $R^4$ may be bonded to each other to form a cycloalkyl group and this cycloalkyl group may have an aromatic ring or heterocyclic ring as a result of condensation reaction; $R^5$ represents an optionally substituted alkyl group, an optionally substituted cycloalkyl group, an optionally substituted aryl group, or an optionally substituted heterocycle or represents an ester-protective group in general use; and $R^6$ represents a hydrogen atom, an optionally substituted alkyl group, an optionally substituted cycloalkyl group, an optionally substituted aryl group, or an optionally substituted heterocycle or represents an amino-acid-protective group in general use, to obtain an amino acid ester carbamate compound represented by the following formula (3):

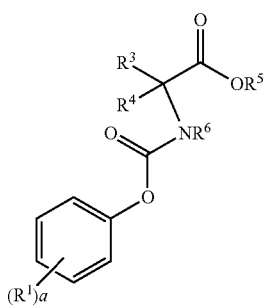

(3)

wherein $R^1$ and a respectively are the same as the $R^1$ and a in formula (1) given above, provided that they may respectively be the $R^2$ and b in formula (1) given above; and $R^3$, $R^4$, $R^5$, and $R^6$ respectively are the same as the $R^3$, $R^4$, $R^5$, and $R^6$ in formula (2);

adding an ester-deprotecting agent to the amino acid ester carbamate compound to thereby obtain an intermediate;

collecting the intermediate to thereby obtain an amino acid carbamate compound represented by the following formula (4):

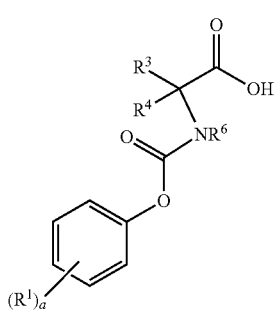

(4)

wherein $R^1$ and a respectively are the same as the $R^1$ and a in formula (1) given above, provided that they may respectively be the $R^2$ and b in formula (1) given above; and $R^3$, $R^4$, and $R^6$ respectively are the same as the $R^3$, $R^4$, and $R^6$ in formula (2);

heating the amino acid carbamate compound to thereby obtain a product; and collecting the product.

It is preferred in the invention that the reaction be conducted in the presence of a reaction promoter.

The reaction promoter preferably comprises at least one member selected from the group consisting of ion-exchange resins, solid basic compounds (such as aluminum oxide, zinc oxide and chromium oxide), inorganic oxides (salts) having surface acid sites (such as zeolites and aluminosilicates) and solid compounds having a function of becoming inactive upon water adsorption (such as molecular sieves, diatomaceous earth and silica gel).

According to the production process of the invention, an amino acid N-carboxyanhydride can be easily obtained in a high yield without using phosgene.

DETAILED DESCRIPTION OF THE INVENTION

The invention is based on the finding that an amino acid N-carboxyanhydride can be obtained by the reaction of an amino acid with a compound represented by formula (1) given above (carbonate compound).

Examples of the amino acid for use in the invention include α-amino acids as major components of proteins, such as glycine, alanine, valine, leucine, isoleucine, phenylalanine, tyrosine, tryptophan, proline, histidine, methionine, cysteine, cystine, arginine, lysine, serine, threonine, glutamic acid, glutamine, aspartic acid, and asparagine. Examples thereof further include ornithine, norleucine, selenocysteine, and cysteinesulfonic acid. Furthermore, β-amino acids, γ-amino acids, and other amino acids can be used according to the intended use.

In the case where the amino acid has two or more carboxyl or amino groups, it is desirable to protect the group(s) other than that participating in the reaction. Although methods for protection are not particularly limited, examples thereof in the case of carboxyl group include a method in which the carboxyl group is substituted with a methyl, ethyl, benzyl, or t-butyl group or the like. In the case of amino group, examples of protection methods include a method in which the amino group is substituted with a carbobenzyloxy, t-butoxycarbonyl, benzoyl, or acetyl group or the like. Examples of preferred carboxyl-protected amino acids include γ-benzyl-L-glutamic acid.

The compound represented by formula (1) (carbonate compound) to be used in the production process of the invention is not particularly limited as long as it has electron-withdrawing substituents. Examples of the electron-withdrawing substituents include acyl groups, alkyloxycarbonyl groups, perfluoroalkyl groups, perchloroalkyl groups, cyano, halogen atoms, and nitro. Alkoxyl groups also are effective depending on substitution positions. Compounds having two or more substituents which are of one kind selected from those or of two or more kinds selected from those are also preferred. Especially preferred of those electron-withdrawing substituents are nitro group and halogen atom substituents from the standpoint of reaction efficiency. Other substituents can coexist with those electron-withdrawing substituents. Examples of such substituents which are optionally present include alkyl groups, cycloalkyl groups, and aryl groups.

Specific examples of the compound represented by formula (1) include bis(4-nitrophenyl) carbonate, bis(2-nitrophenyl) carbonate, bis(2,4-dinitrophenyl) carbonate, bis(2,4,6-trinitrophenyl) carbonate, bis(pentafluorophenyl) carbonate, bis(4-chlorophenyl) carbonate, bis(2,4-dichlorophenyl) carbonate, and bis(2,4,6-trichlorophenyl) carbonate. By using such a carbonate compound having electron-withdrawing substituents, an amino acid N-carboxyanhydride can be obtained in a high yield.

The amount of the compound represented by formula (1) (carbonate compound) to be used in the production process of the invention is not particularly limited. However, the amount thereof is generally 0.1-10 mol, preferably 0.5-5 mol, more preferably 0.8-1.5 mol, per mol of the amino acid or derivative thereof.

A known organic solvent can be used in the invention without particular limitations as long as it does not inhibit the reaction.

Examples of organic solvents usable in the invention include ethers such as tetrahydrofuran, 1,4-dioxane, diethyl ether, and ethylene glycol dimethyl ether; halogenated aliphatic hydrocarbons such as chloroform and dichloromethane; esters such as ethyl acetate and butyl acetate; ketones such as acetone, methyl ethyl ketone, and methyl isobutyl ketone; aromatic hydrocarbons such as benzene, toluene, and xylene; nitriles such as acetonitrile and propinonitrile; carbonates such as dimethyl carbonate; aliphatic hydrocarbons such as hexane and petroleum ethers; and halogenated aromatic hydrocarbons such as chlorobenzene and dichlorobenzene. The use of an organic solvent is not essential, and the amount thereof is not particularly limited. Those solvents may be used singly or as a mixture of two or more thereof.

Reaction conditions in the production process of the invention are not particularly limited. The reaction can usually be conducted in the air. It is, however, desirable to perform the reaction in an inert gas atmosphere such as argon or nitrogen because the compounds used and the product may decompose by the action of water, This reaction can be conducted at any of ordinary pressure, a reduced pressure, and an elevated pressure. It is preferred to select a reaction temperature in the range of generally from −78 to 120° C., preferably from −10 to 100° C. A reaction time of generally 0.1-100 hours is generally required.

The reaction can be accelerated by adding a reaction promoter such as, e.g. a solid compound or an adsorbent. The reaction promoter is not particularly limited. Examples thereof include ion-exchange resins, solid basic compounds, such as aluminum oxide, zinc oxide, and chromium oxide, inorganic oxides (salts) having surface acid sites, such as zeolites and aluminosilicates, and solid compounds having the function of becoming inactive upon water adsorption, such as molecular sieves, diatomaceous earth, and silica gel. Such reaction promoters can be used singly or in combination of two or more thereof. It is thought that when a reaction promoter is used, it removes the water present in a slight amount in the reaction system to thereby highly accelerate the reaction in the invention.

The amount of the reaction promoter to be used is not particularly limited. However, it may be 1-1,000 parts by weight, preferably 10-200 parts by weight, per 100 parts by weight of the amino acid or derivative thereof.

The reaction may be conducted in the presence of a Lewis acid. The Lewis acid is not particularly limited. Examples thereof include titanium tetraisopropoxide, lanthanum trifluoromethanesulfonate, and tris(pentafluorophenyl)borane. Although the amount of the Lewis acid to be used is not particularly limited, it may be 0.05-5 mol, preferably 0.1-1 mol, per mol of the amino acid or derivative thereof.

By conducting the reaction under the reaction conditions described above, an amino acid N-carboxyanhydride is yielded.

The amino acid N-carboxyanhydride yielded is purified by a method in general use, such as, e.g., recrystallization or column chromatography.

In the case of an amino acid having poor solubility in organic solvents, the following synthesis method may be used. That ester of the amino acid which is represented by formula (2) is reacted with a carbonate compound represented by formula (1) to obtain an amino acid ester carbamate compound represented by formula (3). This carbamate compound is subjected to deesterification as shown in formula (4) and then to cyclization to thereby obtain an amino acid N-carboxyanhydride. This process is preferred because it attains a high yield.

The amino acid ester represented by formula (2) is not particularly limited. Use can be made of one obtained by causing a basic compound, e.g., an amine, to act on an amino acid ester acid salt such as an amino acid ester hydrochloride. Examples of the amino acid ester acid salt include amino acid ester hydrochlorides, amino acid ester sulfates, and amino acid ester p-toluenesulfonates. The amino acid ester represented by formula (2) to be used preferably is a t-butyl ester because deprotection from this ester is easy. Examples of the amine include triethylamine, pyridine, and imidazole.

The deprotecting agent for use in the production process of the invention is not particularly limited. Examples thereof include trifluoroacetic acid, hydrochloric acid, sodium hydroxide, and potassium hydroxide.

Conditions for the cyclization reaction in the production process of the invention are not particularly limited. The reaction can usually be conducted in the air. It is, however, desirable to perform the reaction in an inert gas atmosphere such as argon or nitrogen because the compounds used and the product may decompose by the action of water. This reaction can be conducted at any of ordinary pressure, a reduced pressure, and an elevated pressure It is preferred to select a reaction temperature in the range of generally from −78 to 120° C., preferably from −10 to 100° C. A reaction time of generally 0.1-100 hours is generally required. This reaction may be conducted in the presence of a Lewis acid. The Lewis acid is not particularly limited. Examples thereof include titanium tetraisopropoxide, lanthanum trifluoromethanesulfonate, and tris(pentafluorophenyl)borane.

By conducting the reaction under the reaction conditions described above, an amino acid N-carboxyanhydride is yielded.

The amino acid N-carboxyanhydride yielded is purified by a method in general use, such as, e.g., recrystallization or column chromatography.

EXAMPLES

The invention will be illustrated in greater detail by reference to the following Examples, but the invention should not be construed as being limited thereto.

Example 1

(Synthesis of N-Carboxyphenylalanine Anhydride)

Into a two-neck round-bottom flask having a capacity of 25 mL and equipped with a Dimroth condenser were introduced 165 mg (1 mmol) of phenylalanine and 10 mL of tetrahydrofuran in a nitrogen atmosphere. To the resultant solution was added 304 mg (1 mmol) of bis(4-nitrophenyl) carbonate, The mixture was stirred at 60° C. for 27 hours.

This reaction mixture was analyzed by NMR spectroscopy using dioxane as an internal reference. As a result, it was found that N-carboxyphenylalanine anhydride had been obtained in a yield of 13%. Furthermore, this reaction mixture was subjected to column isolation to obtain N-carboxyphenylalanine anhydride in an amount of 19 mg (isolation yield, 10%).

Spectral data for the N-carboxyphenylalanine anhydride: $^1$H NMR (CDCl$_3$) δ: 2.98-3.30 (m, 2H), 4.52-4.55 (m, 1H, —CH<), 6.21 (brs, 1H, —NH—), 7.17-7.38 (m, 5H). $^{13}$C NMR (CDCl$_3$) δ: 37.76, 58.80, 127.98, 129.16, 129.20, 133.81, 151.88, 168.65.

Reference literature for N-carboxyphenylalanine anhydride: *Macromolecules,* 2004, 37, 251

Example 2

(Synthesis of N-Carboxyphenylalanine Anhydride)

Into a two-neck round-bottom flask having a capacity of 25 mL and equipped with a Dimroth condenser were introduced 165 mg (1 mmol) of phenylalanine and 10 mL of tetrahydrofuran in a nitrogen atmosphere. To the resultant solution was added 394 mg (1 mmol) of bis(2,4-dinitrophenyl) carbonate. The mixture was stirred at 60° C. for 91 hours.

This reaction mixture was analyzed by NMR spectroscopy using dioxane as an internal reference. As a result, it was ascertained that N-carboxyphenylalanine anhydride had been obtained in a yield of 100%.

Example 3

(Synthesis of N-Carboxyphenylalanine Anhydride)

Into a two-neck round-bottom flask having a capacity of 25 mL and equipped with a Dimroth condenser were introduced 165 mg (1 mmol) of phenylalanine and 10 mL of tetrahydrofuran in a nitrogen atmosphere. To the resultant solution was added 396 mg (1 mmol) of bis(pentafluorophenyl) carbonate. The mixture was stirred at 60° C. for 60 hours.

This reaction mixture was analyzed by NMR spectroscopy using dioxane as an internal reference. As a result, it was ascertained that N-carboxyphenylalanine anhydride had been obtained in a yield of 56%.

Example 4

(Synthesis of N-Carboxyisoleucine Anhydride)

Into a two-neck round-bottom flask having a capacity of 25 mL and equipped with a Dimroth condenser were introduced 131 mg (1 mmol) of isoleucine and 10 mL of tetrahydrofuran in a nitrogen atmosphere. To the resultant solution was added 304 mg (1 mmol) of bis(4-nitrophenyl) carbonate The mixture was stirred at 60° C. for 67 hours.

This reaction mixture was analyzed by NMR spectroscopy using dioxane as an internal reference. As a result, it was found that N-carboxyisoleucine anhydride had been obtained in a yield of 32%. Furthermore, this reaction mixture was subjected to column isolation to obtain N-carboxyisoleucine anhydride in an amount of 44 mg (isolation yield, 28%).

Spectral data for the N-carboxyisoleucine anhydride: $^1$H NMR (CDCl$_3$) δ: 0.97 (t, J=7.4 Hz, 3H), 1.06 (d, J=6.8 Hz, 3H), 1.32-1.56 (m, 2H), 1.93-2.03 (m, 1H), 4.28-4.30 (m, 1H, —CH<), 7.13 (brs, 1H, —NH—). $^{13}$C NMR (CDCl$_3$) δ: 11.29, 14.72, 24.18, 37.27, 62.38, 153.51, 168.85.

Reference literature for N-carboxyisoleucine anhydride: *J. Am. Chem. Soc.,* 2001, 123, 12919.

Example 5

(Synthesis of N-Carboxyisoleucine Anhydride)

Into a two-neck round-bottom flask having a capacity of 25 mL and equipped with a Dimroth condenser were introduced 131 mg (1 mmol) of isoleucine and 10 mL of tetrahydrofuran in a nitrogen atmosphere. To the resultant solution was added 394 mg (1 mmol) of bis(2,4-dinitrophenyl) carbonate. The mixture was stirred at 60° C. for 49 hours.

This reaction mixture was analyzed by NMR spectroscopy using dioxane as an internal reference. As a result, it was ascertained that N-carboxyisoleucine anhydride had been obtained in a yield of 90%.

Example 6

(Synthesis of N-Carboxyisoleucine Anhydride)

Into a two-neck round-bottom flask having a capacity of 25 mL and equipped with a Dimroth condenser were introduced 131 mg (1 mmol) of isoleucine and 10 mL of tetrahydrofuran in a nitrogen atmosphere. To the resultant solution was added 396 mg (1 mmol) of bis(pentafluorophenyl) carbonate. The mixture was stirred at 60° C. for 42 hours.

This reaction mixture was analyzed by NMR spectroscopy using dioxane as an internal reference. As a result, it was ascertained that N-carboxyisoleucine anhydride had been obtained in a yield of 69%.

Example 7

(Synthesis of N-Carboxy-γ-benzyl-α-glutamic Acid Anhydride)

Into a two-neck round-bottom flask having a capacity of 25 mL and equipped with a Dimroth condenser were introduced 237 mg (1 mmol) of γ-benzyl-L-glutamic acid and 10 mL of tetrahydrofuran in a nitrogen atmosphere. To the resultant solution was added 304 mg (1 mmol) of bis(4-nitrophenyl) carbonate. The mixture was stirred at 60° C. for 72 hours.

This reaction mixture was analyzed by NMR spectroscopy using dioxane as an internal reference. As a result, it was found that N-carboxy-γ-benzyl-α-glutamic acid anhydride had been obtained in a yield of 39%. Furthermore, this reaction mixture was subjected to column isolation to obtain N-carboxy-γ-benzyl-α-glutamic acid anhydride in an amount of 76 mg (isolation yield, 29%).

Spectral data for the N-carboxy-γ-benzyl-α-glutamic acid anhydride: $^1$H NMR (CDCl$_3$) δ: 2.07-2.31 (m, 2H), 2.57-2.61 (m, 2H), 4.37-4.40 (m, 1H, >CH—), 5.13 (s, 2H), 6.69 (brs, 1H, —NH—), 7.26-7.40 (m, 5H) $^{13}$C NMR (CDCl$_3$) δ: 26.85, 29.75, 56.87, 67.07, 128.33, 128.55, 128.68, 135.18, 151.92, 169.34, 172.35.

Reference literature for N-carboxy-γ-benzyl-α-glutamic acid anhydride: *Macromolecules,* 2004, 37, 251.

Example 8

(Synthesis of N-Carboxy-γ-benzyl-α-glutamic Acid Anhydride)

Into a two-neck round-bottom flask having a capacity of 25 mL and equipped with a Dimroth condenser were introduced 237 mg (1 mmol) of γ-benzyl-L-glutamic acid and 10 mL of tetrahydrofuran in a nitrogen atmosphere. To the resultant solution was added 394 mg (1 mmol) of bis(2,4-dinitrophenyl) carbonate. The mixture was stirred at 60° C. for 84 hours. This reaction mixture was analyzed by NMR spectroscopy using dioxane as an internal reference. As a result, it was ascertained that N-carboxy-γ-benzyl-α-glutamic acid anhydride had been obtained in a yield of 98%.

Example 9

(Synthesis of N-Carboxy-γ-benzyl-α-glutamic Acid Anhydride)

Into a two-neck round-bottom flask having a capacity of 25 mL and equipped with a Dimroth condenser were introduced 237 mg (1 mmol) of γ-benzyl-L-glutamic acid and 10 mL of tetrahydrofuran in a nitrogen atmosphere. To the resultant solution was added 396 mg (1 mmol) of bis(pentafluorophenyl) carbonate. The mixture was stirred at 60° C. for 149 hours. This reaction mixture was analyzed by NMR spectroscopy using dioxane as an internal reference. As a result, it was ascertained that N-carboxy-γ-benzyl-α-glutamic acid anhydride had been obtained in a yield of 77%.

Example 10

Into a two-neck round-bottom flask having a capacity of 25 mL and equipped with a Dimroth condenser were introduced 237 mg (1 mmol) of γ-benzyl-L-glutamic acid, 237 mg of molecular sieve 4A, and 10 mL of tetrahydrofuran in a nitrogen atmosphere. To the resultant solution was added 394 mg (1 mmol) of bis(2,4-dinitrophenyl) carbonate. The mixture was stirred at 60° C. for 2 hours. This reaction mixture was analyzed by NMR spectroscopy using dioxane as an internal reference. As a result, it was ascertained that N-carboxy-γ-benzyl-α-glutamic acid anhydride had been obtained in a yield of 100%.

Example 11

(Synthesis of N-Carboxyphenylalanine Anhydride)

Into a round-bottom flask having a capacity of 25 mL were introduced 257 mg (1 mmol) of phenylalanine t-butyl ester hydrochloride and 10 mL of tetrahydrofuran. To the resultant solution was added 101 mg (1 mmol) of triethylamine. The mixture was stirred at room temperature for 1 hour. This reaction mixture was filtered through a syringe filter to obtain a tetrahydrofuran solution of phenylalanine t-butyl ester. To this solution was added 304 mg (1 mmol) of bis(4-nitrophenyl) carbonate. The mixture was stirred at room temperature for 3 hours. This reaction mixture was analyzed by NMR spectroscopy using dioxane as an internal reference. As a result, it was found that N-(4-nitrophenoxycarbonyl)phenylalanine t-butyl ester had been obtained in a yield of 97%. Furthermore, this reaction mixture was subjected to column isolation to obtain N-(4-nitrophenoxycarbonyl)phenylalanine t-butyl ester in an amount of 352 mg (isolation yield, 91%).

Spectral data for the N-(4-nitrophenoxycarbonyl)phenylalanine t-butyl ester: $^1$H NMR (CDCl$_3$) δ: 1.45 (s, 9H), 3.19-3.22 (m, 2H), 4.55-4.61 (m, 1H), 5.62-5.63 (m, 1H), 7.21-7.35 (m, 7H), 8.22-8.25 (m, 2H).

Reference literature for N-(4-nitrophenoxycarbonyl)phenylalanine t-butyl ester: JP-A-9-118662

In a nitrogen atmosphere, 193 mg (0.5 mmol) of the N-(4-nitrophenoxycarbonyl)phenylalanine t-butyl ester and 5 mL of trifluoroacetic acid were introduced into a round-bottom flask having a capacity of 10 mL. The contents were stirred at room temperature for 1 hour. This reaction mixture was concentrated under reduced pressure with a vacuum pump and then analyzed by NMR spectroscopy using dioxane as an internal reference. As a result, it was found that N-(4-nitrophenoxycarbonyl)phenylalanine had been obtained in a yield of 96%. Furthermore, this reaction mixture was subjected to column isolation to obtain N-(4-nitrophenoxycarbonyl)phenylalanine in an amount of 160 mg (isolation yield, 97%).

Spectral data for the N-(4-nitrophenoxycarbonyl)phenylalanine: $^1$H NMR (CDCl$_3$) δ: 3.18-3.34 (m, 2H), 4.76-4.81 (m, 1H), 5.51-5.53 (m, 1H), 7.23-7.40 (m, 7H), 8.23-8.27 (m, 2H).

Reference literature for N-(4-nitrophenoxycarbonyl)phenylalanine: *Chem. Lett.,* 2003, 32, 830.

Into a two-neck round-bottom flask having a capacity of 10 mL and equipped with a Dimroth condenser were introduced 99 mg (0.3 mmol) of the N-(4-nitrophenoxycarbonyl)phenylalanine and 3 mL of chloroform-d in a nitrogen atmosphere. The mixture was refluxed for 128 hours. This reaction mixture was analyzed by NMR spectroscopy using dioxane as an internal reference. As a result, it was found that N-carboxyphenylalanine anhydride had been obtained in a yield of 57% in a reaction time of 96 hours. Furthermore, this reaction mixture was subjected to column isolation to obtain N-carboxyphenylalanine anhydride.

According to the production process of the invention, an amino acid N-carboxyanhydride can be easily obtained in a high yield without using phosgene. The amino acid N-carboxyanhydride thus obtained can be expected to be utilized as a raw material for synthetic poly(amino acid) s useful in the industrial fields of, e.g., cosmetics, medical/medicinal products, and various functional chemical products.

While the present invention has been described in detail and with reference to specific embodiments thereof, it will be apparent to one skilled in the art that various changes and modifications can be made therein without departing from the spirit and scope thereof.

This application is based on Japanese Patent Application No. 2005-203769 filed Jul. 13, 2005, the contents thereof are being herein incorporated by reference.

What is claimed is:

1. A process for producing an amino acid N-carboxyanhydride having the following formula (5):

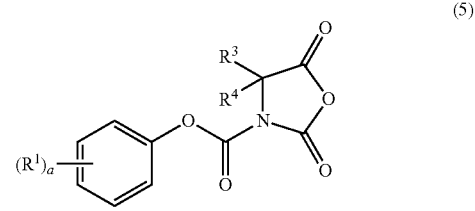

(5)

which comprises reacting an amino acid with a compound represented by the following formula (1):

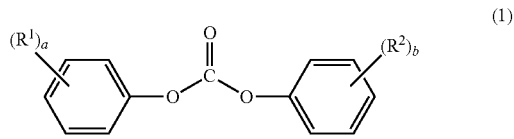

(1)

wherein R$^1$ and R$^2$ represent the same or different electron-withdrawing substituents and each independently are an optionally substituted perfluoroalkyl group, an optionally substituted perchloroalkyl group, a halogen atom, or a nitro group; and a and b are the same or different and each are an integer of 1, 2, 3, 4 or 5, and wherein $R^3$ and $R^4$ each independently is a hydrogen atom or an optionally substituted alkyl group.

2. The process for producing an amino acid N-carboxyanhydride according to claim 1, which comprises:

reacting the compound represented by formula (1) with an amino acid ester represented by the following formula (2):

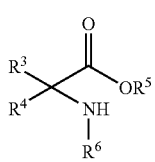

(2)

wherein $R^3$ and $R^4$ are the same as the $R^3$ and $R^4$, respectively, in formula (5); and $R^5$ and $R^6$ are independently an optionally substituted alkyl group, to obtain an amino acid ester carbamate compound represented by the following formula (3):

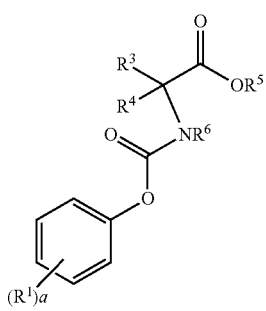

(3)

wherein $R^1$ and a respectively are the same as the $R^1$ and a in formula (1), provided that they may respectively be the $R^2$ and b in formula (1); and $R^3$, $R^4$, $R^5$, and $R^6$ respectively are the same as the $R^3$, $R^4$, $R^5$, and $R^6$ in formula (2);

adding an ester-deprotecting agent to the amino acid ester carbamate compound;

to thereby obtain an amino acid carbamate compound represented by the following formula (4):

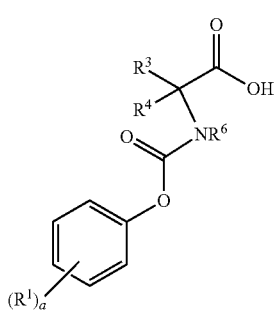

(4)

wherein $R^1$ and a respectively are the same as the $R^1$ and a in formula (1), provided that they may respectively be the $R^2$ and b in formula (1); and $R^3$, $R^4$, and $R^6$ respectively are the same as the $R^3$, $R^4$, and $R^6$ in formula (2); and heating the amino acid carbamate compound to thereby obtain the amino acid N-carboxyanhydride.

3. The process for producing an amino acid N-carboxyanhydride of claim 1, wherein the reaction is conducted in the presence of a reaction promoter, wherein the reaction promoter is at least one member selected from the group consisting of an ion-exchange resin, a solid basic compound, a zeolite, an aluminosilicate, a molecular sieve, a diatomaceous earth and a silica gel.

4. The process for producing an amino acid N-carboxyanhydride according to claim 1, wherein the compound represented by formula (1) is selected from the group consisting of bis(4-nitrophenyl) carbonate, bis(2-nitrophenyl) carbonate, bis(2,4-dinitrophenyl) carbonate, bis(2,4,6-trinitrophenyl) carbonate, bis(pentafluorophenyl) carbonate, bis(4-chlorophenyl) carbonate, bis(2,4-dichlorophenyl) carbonate, and bis(2,4,6-trichlorophenyl) carbonate.

5. The process for producing an amino acid N-carboxyanhydride according to claim 1, wherein the compound represented by formula (1) is used in an amount of 0.1-10 mol per mol of the amino acid.

6. The process for producing an amino acid N-carboxyanhydride according to claim 1, wherein the compound represented by formula (1) is used in an amount of 0.5-5 mol per mol of the amino acid.

7. The process for producing an amino acid N-carboxyanhydride according to claim 1, wherein the compound represented by formula (1) is used in an amount of 0.8-1.5 mol per mol of the amino acid.

8. The process for producing an amino acid N-carboxyanhydride according to claim 1, wherein said reacting is carried out in an inert atmosphere.

9. The process for producing an amino acid N-carboxyanhydride according to claim 1, wherein said reacting is carried out at a reaction temperature in the range of −78° C. to 120° C.

10. The process for producing an amino acid N-carboxyanhydride according to claim 1, wherein said reacting is carried out at a reaction temperature in the range of −10° C. to 100° C.

11. The process for producing an amino acid N-carboxyanhydride according to claim 3, wherein the reaction promoter is present in an amount of 1-1,000 parts by weight per 100 parts by weight of the amino acid.

12. The process for producing an amino acid N-carboxyanhydride according to claim 3, wherein the reaction promoter is present in an amount of 10-200 parts by weight per 100 parts by weight of the amino acid.

13. The process for producing an amino acid N-carboxyanhydride according to claim 1, wherein said reacting is carried out in the presence of a Lewis acid selected from the group consisting of titanium tetraisoproxide, lanthanum trifluoromethanesulfonate and tris(pentafluorophenyl) borane.

14. The process for producing an amino acid N-carboxyanhydride of claim 2, wherein the reaction is conducted in the presence of a reaction promoter, wherein the reaction promoter is at least one member selected from the group consisting of an ion-exchange resin, a solid basic compound, a zeolite, an aluminosilicate, a molecular sieve, a diatomaceous earth and a silica gel.

* * * * *